(12) United States Patent
Noh et al.

(10) Patent No.: US 10,765,717 B2
(45) Date of Patent: Sep. 8, 2020

(54) DETOXIFYING COMPOSITION CONTAINING NEW GREEN EXTRACT AS ACTIVE INGREDIENT

(71) Applicant: FAMENITY CO., LTD., Gwacheon-si (KR)

(72) Inventors: Yoo Hun Noh, Seoul (KR); Young Ja Kim, Gwangju (KR); Jeong Min Lee, Yongin-si (KR)

(73) Assignee: FAMENITY CO., LTD., Gwacheon-si (KR)

( * ) Notice: Subject to any disclaimer, the term of this patent is extended or adjusted under 35 U.S.C. 154(b) by 0 days.

(21) Appl. No.: 16/254,712

(22) Filed: Jan. 23, 2019

(65) Prior Publication Data
US 2019/0151389 A1    May 23, 2019

Related U.S. Application Data

(62) Division of application No. 15/524,299, filed as application No. PCT/KR2015/011017 on Oct. 19, 2015, now abandoned.

(30) Foreign Application Priority Data

Nov. 7, 2014   (KR) .......................... 10-2014-0154790

(51) Int. Cl.
*A61K 36/31* (2006.01)
*A23L 33/105* (2016.01)
*A61K 36/28* (2006.01)

(52) U.S. Cl.
CPC ............ *A61K 36/31* (2013.01); *A23L 33/105* (2016.08); *A61K 36/28* (2013.01); *A23V 2002/00* (2013.01)

(58) Field of Classification Search
None
See application file for complete search history.

(56) References Cited

U.S. PATENT DOCUMENTS

2007/0021376 A1*   1/2007   Giampapa .............. A61K 31/10
514/52

OTHER PUBLICATIONS

*Brassica oleracea* var. *acephala* 'Toscano'/Toscano Kale, onlineplantguide.com/Plant-Details/4233/, copyright 2007-2018. (Year: 2019).*
Vessal, et al., Renal Failure, 32:733. (Year: 2010).*
Lemos, et al., Journal of Ethnopharmacology, 138:503. (Year: 2011).*
Clarke, et al., Pharmacol. Res., 64:456. (Year: 2011).*

* cited by examiner

*Primary Examiner* — Michael Barker
(74) *Attorney, Agent, or Firm* — STIP Law Group, LLC

(57) ABSTRACT

The present invention relates to a detoxifying composition containing a new green extract, which is a medicinal herb, as an active ingredient. Thus, toxicities in the human body can be efficiently removed without side effects by activating an enzyme necessary for detoxification.

10 Claims, 7 Drawing Sheets

DETOXIFYING COMPOSITION CONTAINING NEW GREEN EXTRACT AS ACTIVE INGREDIENT

CROSS-REFERENCE TO RELATED APPLICATIONS

This application is a Division of application Ser. No. 15/524,299 filed on May 4, 2017, which in turn claims benefit of International Application No. PCT/KR2015/011017 filed on Oct. 19, 2015, which in turn claims the benefit of Korean Application No. 10-2014-0154790, filed on Nov. 7, 2014, the disclosures of which are incorporated by reference into the present application.

TECHNICAL FIELD

The present invention relates to a detoxifying composition, and more particularly, to a detoxifying composition containing a new green extract as an active ingredient to activate detoxification.

BACKGROUND ART

Toxicities correspond not only to waste products produced by the metabolic processes or various side products produced by activated oxygen or stress, and the like, but also to exotoxins or endotoxins generated by infiltration of bacteria, and toxic substances that plants or animals have.

Recently, interests in the detoxification to remove these toxicities have been increased. Detoxification has a comprehensive meaning referring to preventing hazardous substances from being introduced into the body and promoting the discharge of waste products through the intestines or kidneys, the lungs, the skin, and the like, and specific examples thereof include alcohol detoxification, drug detoxification, metabolic detoxification, and the like. Diets or exercises and foods for the detoxification have been developed, and among them, detoxification through food has been actively studied.

The present inventors have conducted studies on a medicine which becomes a raw material for food for the detoxification, and have confirmed that a new green extract activates the detoxification, thereby completing the present invention.

New green is a type of broccoli of the Brassicaceae family, and is also referred to as toscano. For new green, leaves are usually used for edible use, and new green contains vitamin C, beta carotene, potassium, calcium, phosphorus, and the like, and new green is known to be a highly nutritious plant because the content thereof normally amounts to twice that of vegetables.

Meanwhile, there have been no studies on whether new green has an effect on the detoxification.

DISCLOSURE

Technical Problem

The present invention has been made in an effort to solve the problems, and an object of the present invention is to provide a detoxifying composition containing a new green extract capable of activating enzymes required during detoxification in the human body as an active ingredient.

Technical Solution

The present invention to solve the aforementioned problems has a technical feature to provide a detoxifying food composition containing a new green extract as an active ingredient. Further, the present invention to solve the aforementioned problems has a technical feature to provide a detoxifying food composition containing a complex extract of new green and thistle as an active ingredient.

Advantageous Effects

A detoxifying composition containing a new green extract according to the present invention as an active ingredient can efficiently remove toxicities in the human body without side effects by activating the detoxification.

BEST MODE

Figure 1:
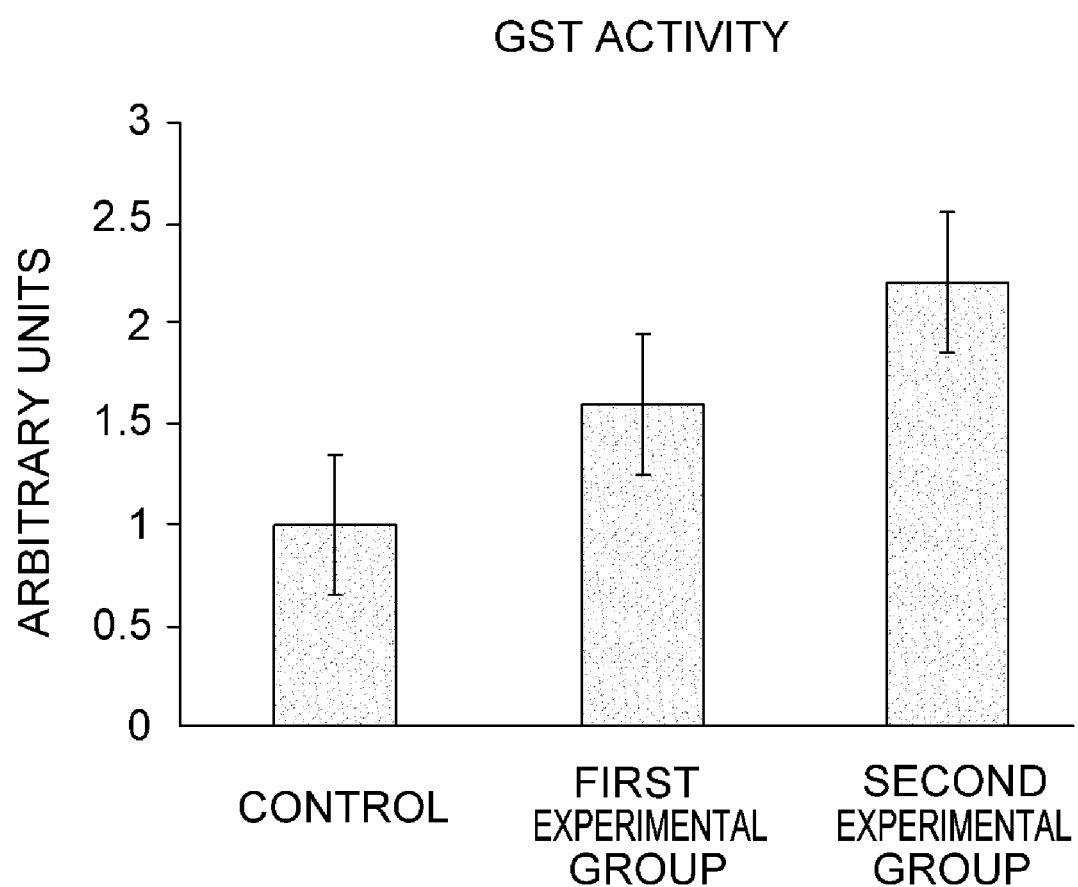
FIG. 1 is a graph illustrating the relative activity of glutathione-S-transferase in Hepa1c1c7 cells.

Before the present invention is described, the meaning of the terms used in the present invention will be described.

In the present specification, the 'extract' has a meaning commonly used as a crude extract in the art, but also includes a meaning of a fractionated product obtained by additionally fractionating the extract in a wide sense. That is, a new green extract includes not only those obtained by using the above-described extraction solvent, but also those obtained by additionally applying a purification process. For example, a fractionation obtained by allowing the extract to pass through an ultrafiltration membrane having a predetermined molecular weight cut-off value, and a fractionation obtained through various purification methods such as separation by means of various chromatography methods (those manufactured for separation according to the size, charge, and hydrophobicity or hydrophilicity) additionally carried out are included in the new green extract of the present invention.

In the present specification, 'including (a new green extract) as an active ingredient' means including an amount sufficient to achieve the efficacy or activity of a new green extract. The present invention is a composition extracted from new green which is a natural plant substance, and has no side effects on the human body even though the composition is administered in excess, and accordingly, the upper limit of the amount of new green extract included in the composition of the present invention may be selected within an appropriate range and carried out by a person skilled in the art.

In the present specification, the 'pharmaceutically effective amount' means an amount of a new green sufficient to achieve the efficacy or activity of a new green extract.

Hereinafter, the composition of the present invention will be described in detail.

The new green extract according to the present invention is extracted by using an organic solvent, and those which may be used as an extraction solvent are as follows. First, examples of those suitable as a polar solvent include (i) water, (ii) alcohol having 1 to 6 carbon atoms (preferably, methanol, ethanol, propanol, butanol, normal-propanol, isopropanol, normal-butanol, 1-pentanol, 2-butoxyethanol or ethylene glycol), (iii) acetic acid, (iv) dimethyl-formamide (DMFO), and (v) dimethyl sulfoxide (DMSO), and the like.

Moreover, examples of those suitable as a non-polar solvent include acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride, methylene chloride, petroleum ether, THF, and the like.

It is preferred that the present invention uses (a) water, (b) an anhydrous or lower alcohol having 1 to 4 carbon atoms (methanol, ethanol, propanol, butanol, and the like), (c) a mixed solvent of the lower alcohol and water, (d) acetone, (e) ethyl acetate, (f) chloroform, (g) butyl acetate, (h) 1,3-butyelene glycol, (i) hexane, (j) diethyl ether, and the like as the extraction solvent, and it is more preferred that for facilitated extraction, the extraction is carried out by treating new green with water, ethanol, or a mixture of water and ethanol.

Further, the new green extract used in the present invention may be prepared in a powder state by an additional process such as distillation under reduced pressure and lyophilization or spray drying.

Therefore, the present invention may prepare an extract by using the aforementioned extraction solvent, and a method for preparing a new green extract will be described below.

1) Preparation of New Green Extract

① New green is sorted and ground, and then an extraction is carried out repeatedly ② by using a solvent selected from water including purified water with a volume amount (v/w %) which is about 1 to 25 times, preferably 7 to 20 times the weight of the ground substance, a lower alcohol having 1 to 4 carbon atoms, such as methanol, ethanol, and butanol, or a mixed solvent thereof, more preferably water, ethanol, or a mixed solvent thereof, ③ at an extraction temperature of 0 to 120° C., preferably 50 to 100° C., ④ for about 1 hour to 10 days, preferably about 2 hours to 8 hours ⑤ by means of an extraction method such as cold brew extraction, hot water extraction, ultrasonic extraction, reflux cooling extraction, or heated extraction, preferably hot water extraction or reflux cooling extraction, ⑥ about one time to ten times, preferably two times to eight times. Moreover, a new green extract is obtained by ⑦ filtering the extract by a filter cloth, ⑧ concentrating the filtrate under vacuum, and then ⑨-① lyophilizing the filtrate or ⑨-② mixing the concentrate with dextrin according to the blending ratio and spray drying the resulting mixture.

2) Preparation of Thistle Complex Extract

① Thistle is sorted and ground, and then an extraction is carried out repeatedly ② by using a solvent selected from water including purified water with a volume amount (v/w %) which is about 1 to 25 times, preferably 7 to 20 times the weight of the ground substance, a lower alcohol having 1 to 4 carbon atoms, such as methanol, ethanol, and butanol, or a mixed solvent thereof, more preferably water, ethanol, or a mixed solvent thereof, ③ at an extraction temperature of 0 to 120° C., preferably 50 to 100° C., ④ for about 1 hour to 10 days, preferably about 2 hours to 8 hours ⑤ by means of an extraction method such as cold brew extraction, hot water extraction, ultrasonic extraction, reflux cooling extraction, or heated extraction, preferably hot water extraction or reflux cooling extraction, and ⑥ about one time to ten times, preferably two times to eight times. Moreover, a new green extract is obtained by ⑦ filtering the extract by a filter cloth, ⑧ concentrating the filtrate under vacuum, and then ⑨-① lyophilizing the filtrate or ⑨-② mixing the concentrate with dextrin according to the blending ratio and spray drying the resulting mixture.

3) Preparation of Complex Extract of New Green and Thistle

The new green extract produced in 1) and the thistle extract produced in 2) are mixed.

Moreover, a new green extract and a complex extract of new green and thistle to be used in an experiment to be described below are prepared by performing a primary extraction by means of a hot water extraction method using purified water with a volume amount which is eight times the weight of the ground substance of new green and thistle as a solvent for 4 hours, performing a secondary extraction by adding purified water with a volume amount which is four times the weight of the ground substance, and then filtering the extract by a filter cloth, concentrating the filtrate under vacuum, and then mixing the concentrate with dextrin at a ratio of 1:1, and spray drying the resulting mixture.

Meanwhile, the new green extract and the complex extract of new green and thistle may be prepared through a subcritical extraction method which extracts the extract by using a subcritical fluid, or a supercritical extraction method which extracts the extract by using a supercritical fluid.

Hereinafter, the effects caused by the new green extract and the complex extract of new green and thistle according to the present invention will be described in detail in the Test Example.

For reference, glutathione S-transferase, quinone reductase, and UDP-glucuronosyl transferase measured in Test Example 1 are enzymes which are involved in phase II in the detoxification process.

Glutathione S-transferase is an enzyme which makes and excretes water-soluble substances which are easily dissolved by bonding electrophilic toxic substances produced during the metabolic process of foreign materials to reduced glutathione (glutathione-SH; GSH), and is present in a large amount in the cytoplasm, and it is revealed that there are a variety of isozymes. Further, the enzyme not only removes activated intermediate metabolites directly responsible for carcinogenesis by using reduced glutathione (GSH) in the organism as a substrate, but also serves to express antioxidant activity.

When foreign toxic substances infiltrate into cells, reduced glutathione has a function of being directly reacted with the foreign toxic substances, or making the foreign toxic substances non-toxic by serving as a substrate of glutathione-S-transferase and glutathione peroxidase to be bonded to the foreign toxic substances (Mitchell, J. R., J. A. Hinson and S. D. Nelson. 1976. Glutathione and drug induced tissue lesion: metabolism and function, pp. 357-367, In I. M. Arias and W. B. Jakoby (eds.), Glutathione. Raven press, New York, N.Y.). Most of the foreign chemicals are metabolized in the cytochrome P450-dependent monooxygenase system, and thus changed into electrophilic products, epoxides, or very highly toxic substances. These substances are directly bonded to reduced glutathione, or are subjected to a conjugation process catalyzed by glutathione-S-transferase, and then are excreted (Molder, P. and B. Jernestiom. 1983. Interaction of glutathione with reactive intermediates. pp. 99-108, In A. Larson, S. Orrenius, A. Holgren and B. Mannervik (eds.), Functions of glutathione: biochemical, physiological, toxicological, and clinical aspects. Raven Press, New York, N.Y.). A reduction in content of reduced glutathione in the body causes liver diseases such as impairment of the secretion of proteins by the hepatocytes, fatty liver, hepatic necrosis, and fibroblast proliferation. Further, when reduced glutathione in the cells is depleted, highly toxic metabolites are produced, and intracellular impairment and outbreak of cancer occur. It was reported by Benson et al. (Benson, A. M. and P. B. Barretto. 1985. Effects of disulfiram, diethydithiocarbamate, bisethylxanthogen, and benzyl isothiocyanate on glutathine activities in mouse organs. Cancer Res. 45, 4219-4223) that compounds including sulfur increase the activity of a toxicity suppressing enzyme such as glutathione-S-transferase or quinone reductase by increasing the content of reduced glutathione in the body, and suppress the production of carcinogens.

It is known that quinone reductase protects cells from the cytotoxicity of a precursor for metabolism by reducing quinone and quinoneimine, and the activity thereof is usually highest in the liver and is also relatively high in the kidneys and the brain, and there is also an effect of suppressing toxic effects, mutagenesis, and the initiation of a carcinogenic process by carcinogenic substances.

Further, quinone reductase uses NAD(P)H as an electron donor, and does not form semiquinone by moving two electrons, and may be called as a representative enzyme among detoxification enzymes due to the protection effects for quinones themselves and the feature to be commonly induced with another cancer prevention enzyme system.

Moreover, glutamic oxaloacetate transaminase, glutamic pyruvate transaminase, alkaline phosphate, lactate dehydrogenase, blood urea nitrogen, uric acid, creatine, total bilirubin, iron, and the like are substances detected in the serum when the amount of toxic substances in the body is increased, and are discharged out of the body in phase III.

Test Example 1: Test on Animal Cells

<1-1> Test Subjects

Hepa1c1c7 cells (ATCC CRL-2026) were suspended in a Dulbecco's Modified Eagle Medium (manufactured by GIBCO Co., Ltd.) containing 10% fetal bovine serum (manufactured by GIBCO Co., Ltd.) and 1% penicillin-streptomycin (manufactured by Invitrogen Corp.) such that the concentration was $4 \times 10^5$ ea/ml, 0.2 ml of the cell suspension was added to each well of a 96-well plate, and then the cells were cultured in a 5% $CO_2$ incubator at 37° C. for 24 hours. And then, the medium was exchanged with a new Dulbecco's Modified Eagle Medium, and then distilled water, new green (50 µg/ml), and a complex extract of new green (25 µg/ml) and thistle (25 µg/ml) were added to a set of the control, a set of the first experimental group, and a set of the second experimental group, respectively, and the cells were cultured for 24 hours. After the culture was completed, the medium was removed, the cells were washed with a phosphate buffer solution, 0.1 ml of a cell lysate was added to the cells, and then the cells were incubated at 37° C. for 10 minutes.

<1-2> Measurement of Activity of Glutathione S-Transferase (Hereinafter, Referred to as 'GST')

155 µl of a reaction solution (1.3 mM glutathione in a potassium phosphate buffer) was added to 25 µl of a cell solution belonging to each group prepared in <1-1>, 20 µl of 10 mM CDNB (2,4-dinitrochlorobenzene, manufactured by Sigma-Aldrich Corp.) being a reaction substrate was added thereto prior to the measurement, and a change in absorbance at a wavelength of 340 nm was measured. Each activity analysis was repeatedly measured three times, and the amount of protein was measured by diluting a sample solution 50 times with a phosphate buffer solution and using a MicroBCA protein analysis kit.

The activity of each GST was calculated by the following equation as a relative value of a control with respect to the GST value, and the results of the relative activity of GST are illustrated in FIG. 1.

GST activity=(maximum rate coefficient of test material added section/amount of protein in test material added section)/(maximum rate coefficient of water added section/amount of protein in water added section)

As illustrated in FIG. 1, a statistically significant improvement in activity was observed, in which the activity of GST of the first experimental group was increased by about 1.6 times as compared to that of the control. Further, the activity of GST of the second experimental group was increased by about 2.2 times as compared to that of the control. Moreover, it can be seen that the complex extract of new green and thistle has a greater effect of increasing the activity than that of new green alone at the same concentration.

<1-3> Measurement of Activity of Quinone Reductase (Hereinafter, Referred to as 'QR')

100 µl of a reaction solution (manufactured by Sigma-Aldrich Corp.) was added to 25 µl of a cell solution belonging to each group prepared in <1-1>. In this case, the presence and absence of a substrate were set, and in the presence of the substrate, menadione (manufactured by Sigma-Aldrich Corp.) was also added to the reaction solution, such that the final concentration became 50 µM. Each activity analysis was carried out repeatedly three times. Further, the QR activity was calculated by the following equation as a QR relative activity with respect to the control, and the results are illustrated in FIG. 2.

QR activity={[(absorbance of test material added section in the presence of substrate)-(absorbance of test material added section in the absence of substrate)]÷(amount of protein in test material added section)}÷{[absorbance of water added section in the presence of substrate]-(absorbance of water added section in the absence of substrate)}÷(amount of protein in water added section)}

Figure 2:
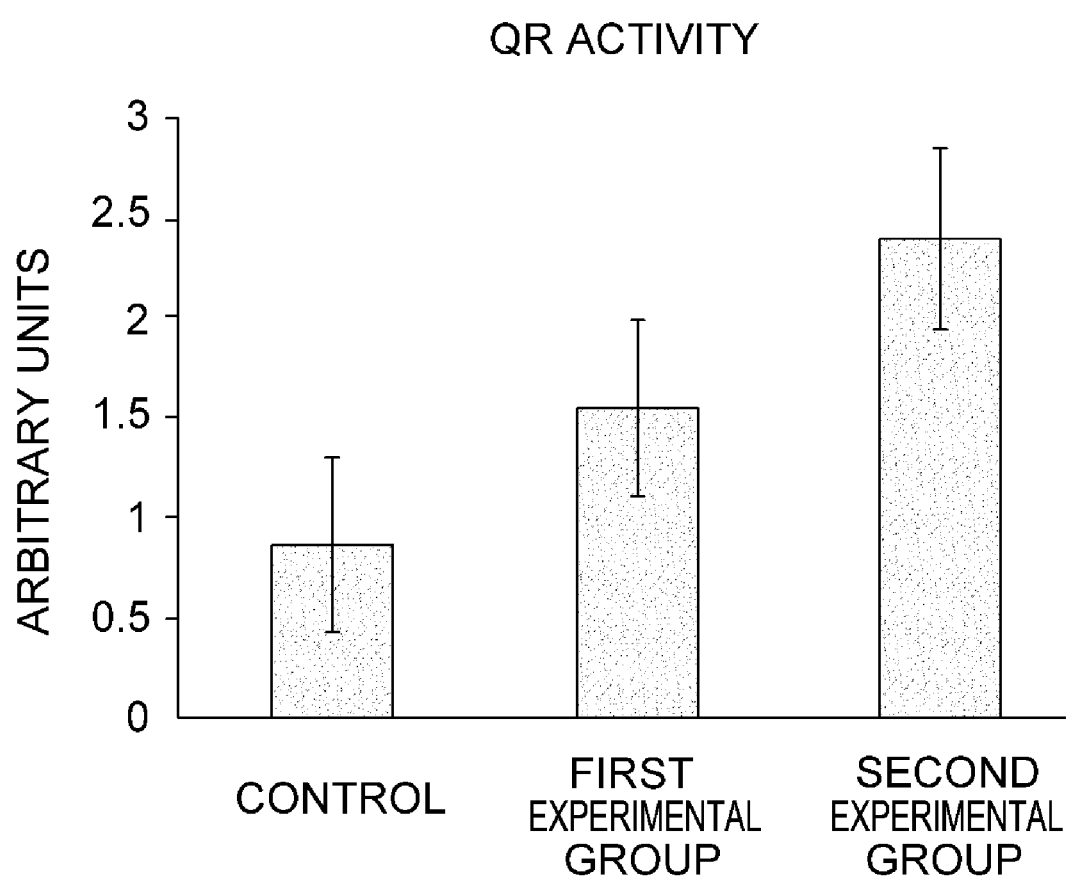
FIG. 2 is a graph illustrating the relative activity of quinone reductase in Hepa1c1c7 cells.

As illustrated in FIG. 2, a statistically significant improvement in activity was observed, in which the activity of the QR enzyme of the first experimental group was increased by about 1.8 times as compared to that of the control, and it was confirmed that the activity of the second experimental group was increased by about 2.8 times as compared to that of the control. Moreover, it can be seen that the complex extract of new green and thistle has a greater effect of increasing the activity than that of new green alone at the same concentration.

<1-4> Measurement of Activity of UDP-Glucuronosyl Transferase (Hereinafter, Referred to as 'UGT')

The UGT activity was measured by partially modifying the method by B. Burchell, P. Weatherill et al. (Methods in Enzymology 77, p. 169 (1981)). During the <1-1> process, a cell solution was prepared by washing cells with a phosphate buffer solution, and then freeze-thawing the cells. 0.2 ml of a reaction solution {0.1 M Tris-HCl (pH7.4), 1 mM MgCl$_2$, 0.02% Triton X-100, 0.15 mM p-nitrophenol (PNP, manufactured by Invitrogen Corp.)} was added to the cell solution, and the resulting mixture was stirred well and incubated in ice for 30 minutes. 80 µl of the enzyme solution was transferred to a 96-well plate, and a fraction obtained by adding 20 µl of 20 mM glucuronic acid (manufactured by Sigma-Aldrich Corp.) to the well and a fraction obtained by adding no glucuronic acid to the well were established and incubated at 37° C. for 1 hour.

Alternatively, a calibration curve was drawn by using a reaction solution PNP at a substrate concentration, and then 100 µl of a 2 M glycine buffer (pH 10.4) was added thereto, and the activity was analyzed by measuring the absorbance at a wavelength of 405 nm. Each activity analysis was carried out three times. Further, the UGT activity is defined as an amount of PNP included with respect to the control and was calculated by the following equation, and the results are illustrated in FIG. 3.

UGT activity=[(amount of PNP in test material added section in the absence of glucuronic acid)−(amount of PNP in test material added section in the presence of glucuronic acid)]÷[(amount of PNP in water added section in the absence of glucuronic acid)−(amount of PNP in water added section in the presence of glucuronic acid)]

Figure 3:
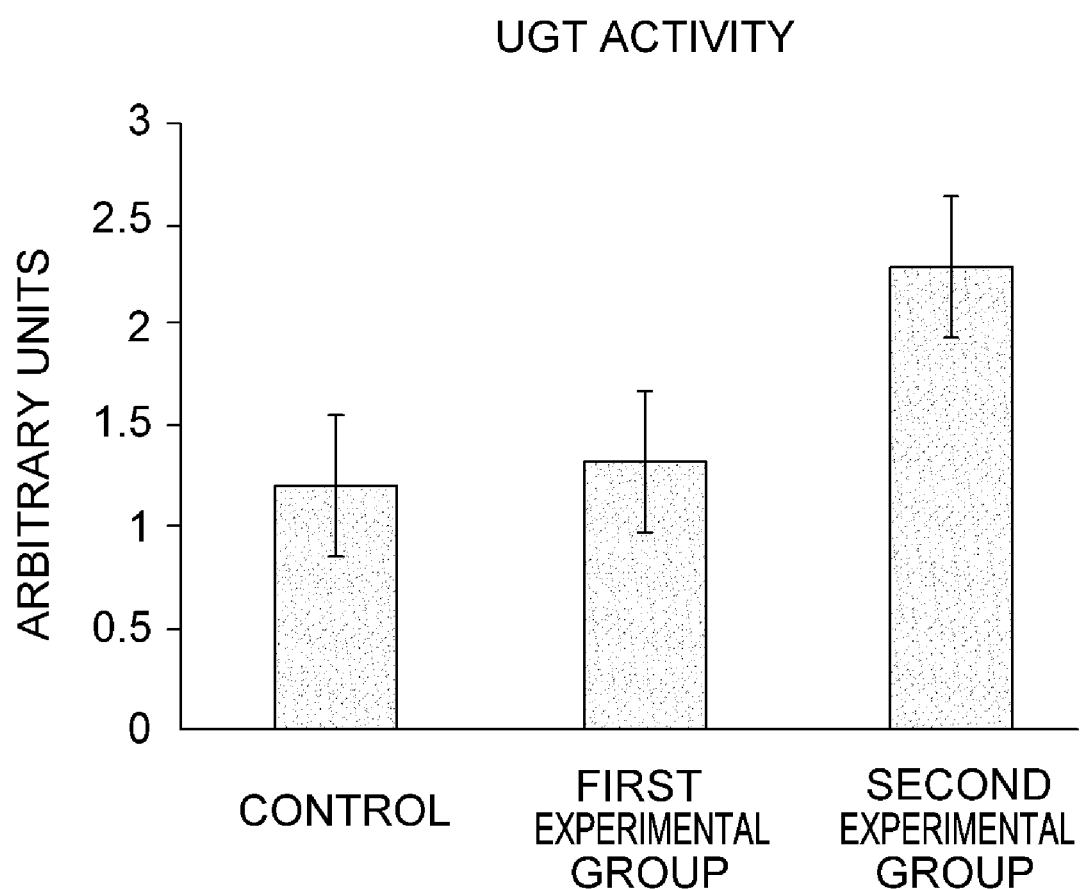
FIG. 3 is a graph illustrating the relative activity of UDP-glucuronosyl transferase in Hepa1c1c7 cells.

As illustrated in FIG. 3, it could be confirmed that the activity of new green was increased by 1.1 times, which was a relatively small increase, but the UGT activity of the complex extract of new green and thistle was significantly increased by about 1.9 times.

<1-5> Measurement of Induction for Expression of Metabolic Toxin Lyase mRNA

<1-5-1> Extraction and Analysis of mRNA in Cells 0.5 ml of RNAiso (manufactured by TaKaRA Bio, Inc.) was added to a cell solution belonging to each group prepared in <1-1>, the resulting mixture was incubated at room temperature for 5 minutes, and then 0.1 ml of chloroform was added thereto, and the resulting mixture was stirred well until the color turned milky white. And then, the mixture was incubated at room temperature for 5 minutes and centrifuged at 10,000 rpm at 4° C. for 15 minutes, and then only the supernatant was collected, 0.25 ml of isopropanol was added to the supernatant, and the resulting mixture was mixed well and incubated at room temperature for 10 minutes. And then, the mixture was centrifuged at 10,000 rpm at 4° C. for 10 minutes, 0.5 ml of the obtained precipitate was lysed, and then the overall aqueous RNA solution was obtained. The reverse transcription reaction and real-time PCR were carried out by using an Exscript RT-PCR Kit (manufactured by TaKaRA Bio, Inc.). A primer specific for transferrin receptor (Tfrc) as a control of all the PCR was used. Moreover, the measurement was carried out by using a Roche system, the activity analysis was carried out each two times, and the amount of mRNA expressed at each analyzed value was calculated as a relative amount of mRNA to be measured for the control.

<1-5-2> Measurement of Expression Amount of GST mRNA

*In order to measure the expression amount of GST mRNA by new green and the complex extract of new green and thistle, the reverse transcription PCR and real-time PCR were carried out by using a primer specific for GST, and the expression amount of mRNA was calculated by using the following equation. The results are illustrated in FIG. 4.

Expression amount of GST mRNA=[(expression amount of GST mRNA in test material added section)÷(expression amount of Tfrc mRNA in test material added section)]÷[(expression amount of GST mRNA in water added section) ÷(expression amount of Tfrc mRNA in water added section)]

Figure 4:
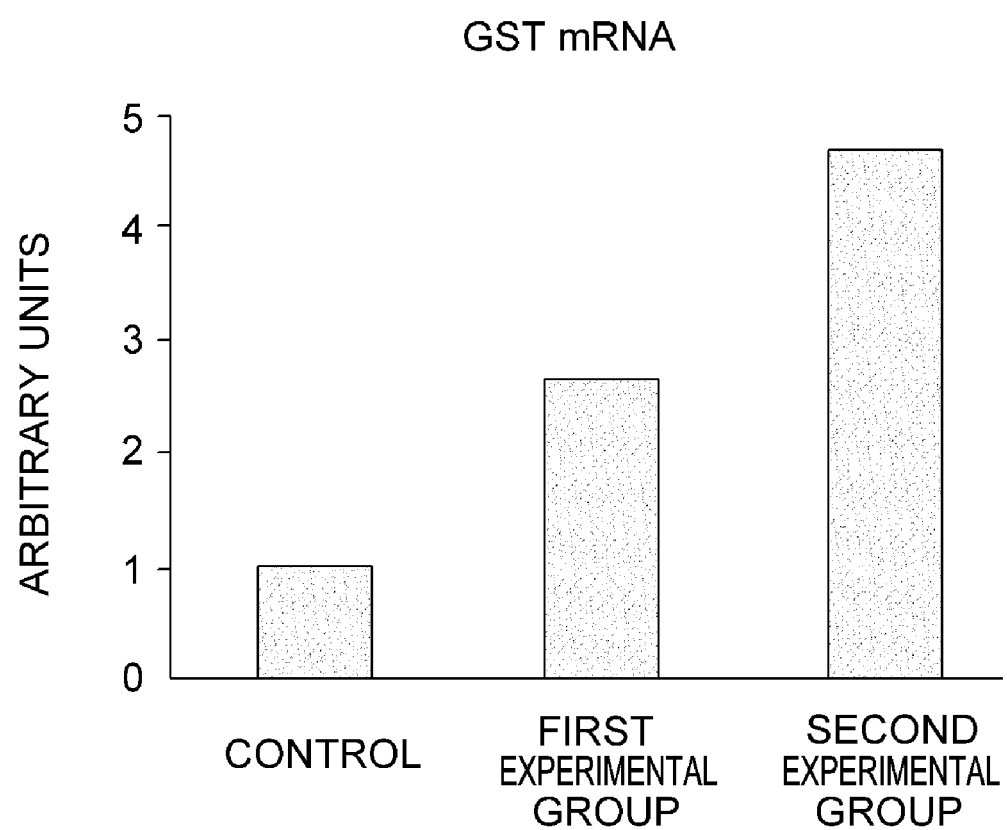
FIG. 4 is a graph illustrating the relative expression amount of glutathione-S-transferase m-RNA in Hepa1c1c7 cells.

As illustrated in FIG. 4, the expression of mRNA of GST, when being treated with new green, was increased by about 2.6 times as compared to that of the control. Further, in the case of the complex extract of new green and thistle, the effect of inducing the expression of GST mRNA, which is better than that of the treatment with thistle alone, was confirmed by confirming an increase in expression amount by about 4.7 times as compared to that of the control.

<1-5-3> Measurement of Amount of QR mRNA Expressed

Figure 5:
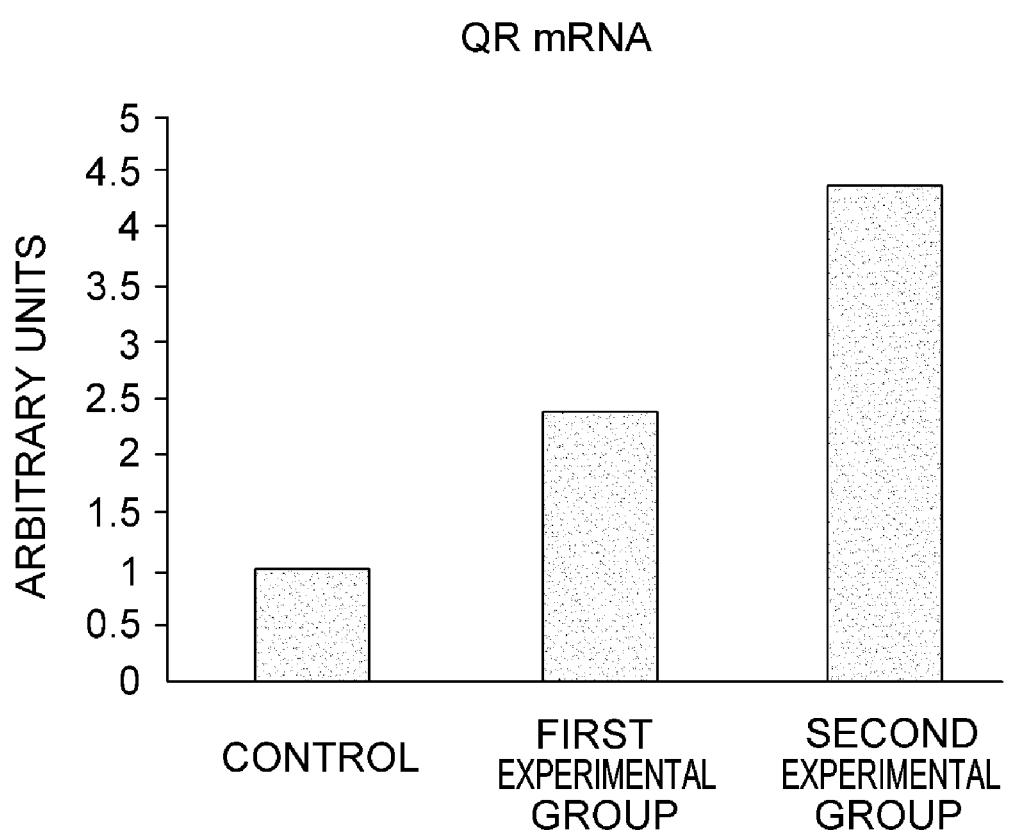
FIG. 5 is a graph illustrating the relative expression amount of quinone reductase in Hepa1c1c7 cells.

In order to measure the expression amount of QR mRNA by new green and the complex extract of new green and thistle, the reverse transcription PCR and real-time PCR were carried out by using a primer specific for GST, and the expression amount of mRNA was calculated by using the following equation. The results are illustrated in FIG. 5.

Expression amount of QR mRNA=[(expression amount of QR mRNA in test material added section)÷(expression amount of Tfrc mRNA in test material added section)]÷[(expression amount of QR mRNA in water added section)÷ (expression amount of Tfrc mRNA in water added section)]

In the result, the expression of mRNA of QR, when being treated with new green, was increased by about 2.4 times as compared to that of the control. Further, in the case of the complex extract of new green and thistle, the effect of inducing the expression of QR mRNA, which is better than that of the treatment with thistle alone, was confirmed by confirming an increase in expression amount by about 4.4 times as compared to that of the control.

<1-5-4> Evaluation of Induction for Expression of UGT mRNA

In order to measure the expression amount of UGT mRNA by new green and the complex extract of new green and thistle, the reverse transcription PCR and real-time PCR were carried out by using a primer specific for UGT, and the expression amount of mRNA was calculated by using the following equation. The results are illustrated in FIG. 6.

Expression amount of UGT mRNA=[(expression amount of UGT mRNA in test material added section)÷(expression amount of Tfrc mRNA in test material added section)]÷[(expression amount of UGT mRNA in water added section) ÷(expression amount of Tfrc mRNA in water added section)]

Figure 6:
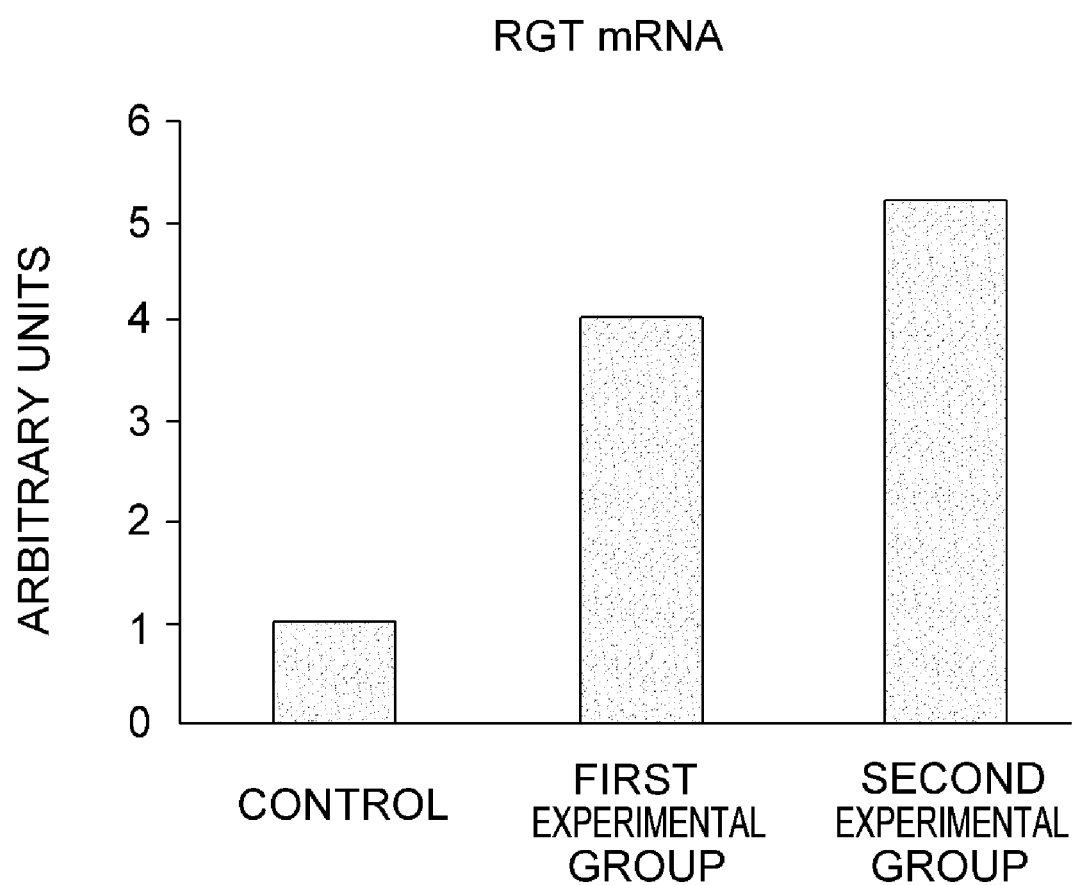
FIG. 6 is a graph illustrating the relative expression amount of UDP-glucuronosyl transferase in Hepa1c1c7 cells.

As illustrated in FIG. 6, the expression of mRNA of QR, when being treated with new green, exhibited an increase in expression amount by about 4 times as compared to that of the control. Further, in the case of the complex extract of new green and thistle, the effect of inducing the expression of QR mRNA, which is better than that of the treatment with new green alone, was confirmed by confirming an increase in expression amount by about 5.2 times as compared to that of the control.

<1-6> Evaluation of Increase in Amount of Glutathione (Hereinafter, Referred to as 'GSH') in Cells In order to evaluate an increase in amount of GSH in hepatocytes by new green and a complex extract of new green and thistle, the evaluation was carried out by partially modifying the method by Clarissa Gerhauser et al. {Cancer Research 57, 271-278(1997)}. During the <1-1> process, cells were washed with a phosphate buffer solution, the freeze-thawing was repeated three times, and then 0.1 ml of Buffer A {a 125 μM sodium phosphate buffer (pH 7.5), 6.3 mM EDTA} was added thereto. 100 μl of a reaction solution {25 mM Tris-HCl (pH 7.4), 1 mM G6P, 30 μm NADP, 2 U/ml G6PDH, 0.25 U/ml glutathione reductase (manufactured by Sigma-Aldrich Corp.), 0.6 mM DTNB)} was added to 25 μl of the cell lysate thus prepared. The resulting mixture was incubated at room temperature for 5 minutes, and then the absorbance at a wavelength of 405 nm was measured. Each activity analysis was carried out three times. As a reference, a solution obtained by continuously diluting 2 to 200 μl of GSH to 2 times instead of the cell lysate was simultaneously measured.

Alternatively, the amount of protein was measured by diluting the cell lysate 50 times with a phosphate buffer solution, and using a MicroBCA protein analysis kit. Alternatively, the amount of GSH was calculated by the following equation as a relative amount of GSH with respect to the control. The results are illustrated in FIG. 7.

GSH activity amount=[(amount of GSH in test material added section)÷(amount of protein in test material added section)]÷[(amount of GSH in water added section)÷(amount of protein in water added section)]

Figure 7:
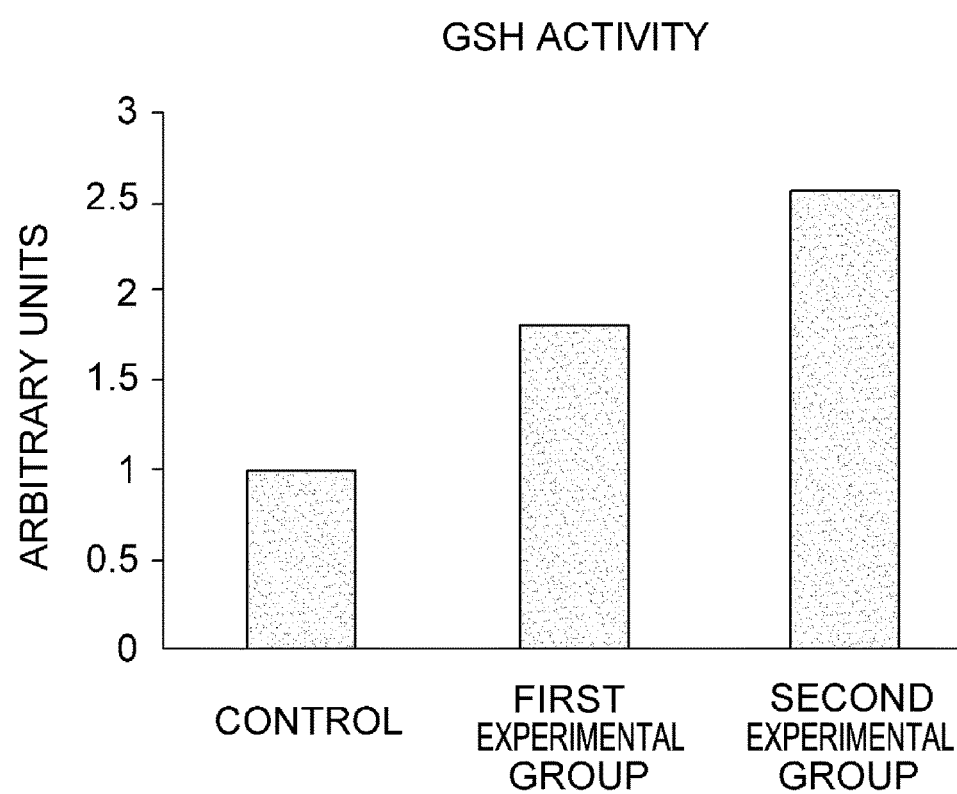
FIG. 7 is a graph illustrating the relative activity of glutathione in Hepa1c1c7 cells.

As illustrated in FIG. 7, it can be seen that the activity of GSH when being treated with new green is increased by about 1.8 times as compared to that of the control. Further, in the case of treatment with a complex extract of new green and thistle, the effect of inducing the GSH activity, which is higher than that of the treatment with new green alone, was confirmed by confirming an increase in GSH activity by about 2.56 times as compared to that of the control.

As described above, it can be seen that the new green extract and the complex extract of new green and thistle according to the present invention activate the detoxification by promoting the action of enzymes which are involved in Phase II during the detoxification.

Test Example 2: Test on Animals

<2-1> Subject and Duration of Study

Studies were performed by purchasing male mice of the Sprague-Dawley lineage, weighing about 150 g from DBL Co., Ltd., and breeding the male mice while maintaining a constant temperature and humidity in a breeding cage. During the experimental period, water and feed were freely fed, and in this case, all the instruments such as water bottles, feeding bowls, and breeding case used were washed with a 0.4%-EDTA solution in order to prevent pollution with heavy metals, rinsed with deionized water, dried, and then used.

After a 7-day adjustment period, the mice to be tested were randomly divided, and 10 mice were each allocated to a normal control, a negative control, a first experimental group, and a second experimental group. Lead (Pb) and cadmium (Cd) were used in order to cause toxicity to the mice to be tested. As lead acetate and cadmium sulfide, special grade-reagents from Junsei Chemical Co. were used, lead and cadmium were adjusted to have a concentration of 50 ppm and 25 ppm, respectively by diluting each of the reagents, and 1 ml of each reagent was intraperitoneally administered to the negative control, the first experimental group, and the second experimental group at 5 o'clock in the afternoon every day for 17 days. Instead of administration of heavy metals to the normal control, 1 ml of physiological saline was intraperitoneally administered to the normal control at 5 o'clock in the afternoon every day. The exposure to heavy metals and hepatotoxin lyase were quantified by collecting blood prior to and after administration of heavy metals.

Moreover, simultaneously, the new green extract and the complex extract of new green and thistle (ratio of 7:3) in the Example were orally administered at 52 mg/day·kg to the first experimental group and the second experimental group, respectively at 5 o'clock in the afternoon every day, and the same volume of physiological saline was orally administered to the normal control and the negative control at the same hour. The concentrations of the new green and the complex extract of new green and thistle were an amount equal to an intake of 500 mg/day·kg based on a 60 kg adult.

<2-2> Decomposition of Heavy Metals and Toxins and Discharge Test Through Clinical Chemical Test of Serum Blood was collected from the femoral vein of the mice to be tested in <2-1> at 5 o'clock in the afternoon the next day after the administration, and then transferred to a tube treated with heparin, and centrifuged in a centrifuge (2,500 rpm, 4° C.) for 15 minutes, thereby separating the plasma.

Moreover, the following ingredients from the separated plasma were identified through each clinical chemical test.

Glutamic Oxaloacetate Transaminase (Hereinafter, Referred to as 'GOT')

Aspartic acid and α-ketoglutaric acid are converted into oxaloacetic acid and L-glutamic acid, respectively by the action of GOT in the serum, and again, oxaloacetic acid produces maleate due to the action of MDH in the presence of coenzyme NADH. Accordingly, when NADH was oxidized to NAD+, the GOT was measured by means of an automatic analyzer (manufactured by Molecular Device Inc.) by using a kit (manufactured by Boehringer Mannheim Co.) using a principle of measuring a decrease in absorbance at a wavelength of 340 nm.

Glutamic Pyruvate Transaminase (Hereinafter, Referred to as 'GPT')

L-alanine and α-ketoglutamic acid were converted into pyruvate and L-glutamic acid, respectively by the action of GPT in the serum, and the produced pyruvate produces lactic acid due to the action of LDH in the presence of coenzyme NADH. Accordingly, when NADH was oxidized to NAD+, the GPT was measured by means of an automatic analyzer (manufactured by Molecular Device Inc.) by using a kit (manufactured by Boehringer Mannheim Co.) which uses a principle of measuring a decrease in absorbance at a wavelength of 340 nm.

Alkaline Phosphatase (Hereinafter, Referred to as 'ALP')

P-nitrophenyl phosphate was used as a substrate, a color was developed by using a kit (ALP, manufactured by Boehringer Mannheim Co.) which uses an IFCC principle of exhibiting the yellow color when P-nitrophenol and NaOH are acted, and the ALP was measured by an automatic analyzer (manufactured by Molecular Device Inc.).

Lactate Dehydrogenase (LDH)

A color was developed by using an LDH kit (manufactured by Boehringer Mannheim Co.) which uses a principle in which when the serum is added to a buffered pyruvate substrate and $NADH_2$, and then the resulting mixture is incubated, the amount of pyruvic acid is decreased and lactic acid and NAD+ are produced by the LDH in the serum, and the LDH was measured by an automatic analyzer (manufactured by Molecular Device Inc.).

Blood Urea Nitrogen (Hereinafter, Referred to as 'BUN')

The concentration of blood urea nitrogen in the serum was measured by means of an automatic analyzer by using a urea kit (manufactured by Boehringer Mannheim Co.).

Uric Acid

A color was developed by using a kit (manufactured by Boehringer Mannheim Co.), and the concentration of uric acid in the serum was measured by means of an automatic analyzer (manufactured by Molecular Device Inc.).

Creatine

Since creatine forms picric acid and colored compounds in an alkaline solution, a color was developed by using a kit (manufactured by Boehringer Mannheim Co.) which uses a principle of obtaining the concentration by measuring the formation rate, and creatine was measured by an automatic analyzer (manufactured by Molecular Device Inc.).

Total Bilirubin

A color was developed by using a kit (Bil-T, manufactured by Boehringer Mannheim Co., Germany) according to the DPD method principle, and then the concentration was obtained by using an automatic analyzer (manufactured by Molecular Device Inc.).

Iron

Serum was wet-digested, and measured by A.A.S.

The results were exhibited as an average and a standard deviation, the statistical processing used a Student's t-test for verification of the significance of the results, $p<0.05$ was considered and marked as significant, and the results are shown in [Table 1].

ALP is pathologically increased in hepatic insufficiency, bone disease, jaundice, and the like, and is decreased in toxic substance poisoning or chronic nephritis. The normal concentration of ALP in the mice to be tested is 14 to 48 unit/l. As shown in Table 1, the concentration of ALP in the case of the negative control was significantly increased as compared to that of the normal control. In contrast, in the first experimental group, the concentration of ALP was increased by a width close to the normal range, and in the second experimental group, the concentration of ALP was slightly increased, but was measured within the normal range.

LDH is distributed in liver, heart, skeletal muscle, kidneys, and the like, and is increased in heart diseases, liver disorders, and kidney disorders. The normal concentration of LDH in the mice to be tested is 167 to 1,428 unit/l. In the case of the negative control, it can be seen that the activity of LDH is within the normal range, but the activity of LDH is increased by about two times as compared to that of the normal control. In contrast, it can be seen that in the case of the first experimental group, the activity of LDH was increased by a significantly small width, and in the case of the second experimental group, the activity of LDH was increased by a small width closer to that of the normal control.

The BUN is an indicator of kidney function diagnosis, which is increased due to the kidney dysfunction, and the normal concentration of BUN in the mice to be tested is 15 to 21 mg/dl. In the case of the negative control, due to the

TABLE 1

| | GOT (unit/l) | GPT (unit/l) | ALP (unit/l) | LDH (unit/l) | BUN (mg/dl) | Uric acid (mg/dl) | Creatine (mg/dl) | Bilirubin (mg/dl) |
|---|---|---|---|---|---|---|---|---|
| Normal control | 62.12 ± 10.54 | 48.43 ± 11.37 | 28.94 ± 5.75 | 212.23 ± 38.92 | 17.28 ± 2.51 | 1.33 ± 0.48 | 1.14 ± 0.07 | 0.28 ± 0.05 |
| Negative control | 148.34 ± 17.34 | 82.17 ± 15.32 | 59.14 ± 4.85 | 432.03 ± 52.92 | 41.21 ± 2.51 | 1.85 ± 0.58 | 2.76 ± 0.18 | 0.58 ± 0.08 |
| First experimental group | 128.14 ± 15.32 | 61.32 ± 9.84 | 51.32 ± 4.10 | 315.83 ± 52.92 | 34.06 ± 3.07 | 1.62 ± 0.66 | 2.16 ± 0.12 | 0.46 ± 0.011 |
| Second experimental group | 115.32 ± 11.23 | 52.94 ± 11.26 | 39.81 ± 6.25 | 298.72 ± 48.12 | 23.82 ± 2.81 | 1.41 ± 0.52 | 1.68 ± 0.06 | 0.38 ± 0.07 |

The normal GOT and normal GPT activities in the blood are 39 to 111 unit/l and 20 to 61 unit/l, respectively, and GPT is specific for liver and increases in chronic hepatitis, acute hepatitis, fatty liver, alcoholic hepatitis, and liver cancer, and GOT is increased in heart, liver, skeletal, kidney, pancreatic disorders, and the like. In the present experimental results, the concentrations of GOT and GPT of the normal control were 62.12 unit/l and 48.43 unit/l, respectively, which are within a normal range, as shown in Table 1. In contrast, in the case of the negative control into which heavy metals were introduced, it could be confirmed that the concentrations were out of the normal range by showing a statistically significant change in concentration. In contrast, in the case of the first experimental group, the concentrations of GOT and GPT exhibited a statistically significant increase width, respectively. Moreover, in the case of the second experimental group, GOT was slightly increased, but came close to the normal range, and GPT was measured within the normal concentration range.

Through this, it can be seen that administration of heavy metals causes poisoning damages to organs such as liver, and intake of the composition according to the present invention protects the organs from toxins by alleviating or reducing the poisoning phenomenon in the organs of mice exposed to toxins such as heavy metals. In particular, the intake of the complex extract of new green and thistle exhibited better effects than the intake of new green alone.

administration of heavy metals, the concentration of BUN was increased by about three times as compared to that of the normal control group. In contrast, in the case of the first experimental group, the concentration of BUN was measured at a significantly low level by 7.2 mg/dl as compared to that of the negative control, and in the case of the second experimental group, the concentration of BUN was measured at a low level by about 16.4 mg/dl as compared to that of the negative control.

Uric acid is known as a representative indicator which is exponentially increased in gout, kidney toxicity, particularly, mercury poisoning, lead poisoning, and the like. In the case of the negative control, the concentration of uric acid was increased by about 0.52 mg/dl or more as compared to that of the normal control. In contrast, in the case of the first experimental group, the increase width was relatively small, and in the case of the second experimental group, the increase width came close to that of the normal control.

Creatine is also an indicator which is increased similarly to uric acid when the kidney function is poor, and the normal concentration of creatine in the mice to be tested is 0.4 to 1.5 mg/dl. In the case of the negative control, the concentration of creatine was increased to 2.76 mg/dl, whereas in the case of the first experimental group, the increase width was relatively small, and in the case of the second experimental group, the increase width also exceeded the normal range, but exhibited a statistically significantly small increase width as compared to that of the negative control.

Bilirubin is a diagnostic indicator which is significantly increased in poisonous liver disease, hemolytic jaundice, carbon tetrachloride, cadmium poisoning, fasting, and the like, and the normal concentration of bilirubin in the mice to be tested is 0.12 to 0.40 mg/dl. The concentration of bilirubin of the negative control was increased by about two times or more as compared to that of the normal control, but the first experimental group exhibited an increase width which is relatively lower than that of the negative control. Moreover, in the case of the second experimental group, the concentration of bilirubin, which is at a normal level, was measured.

As a result of confirming the detoxification effect of the extract according to the present invention through the biochemical assay of the serum, it can be confirmed that abnormal changes of various biochemical indicators caused by heavy metals may be normalized. It can be expected that the phenomenon occurs through the activity of the toxin decomposition Phase II enzyme because new green and a complex extract of new green and thistle contain various active ingredients such as flavonoid, which may aid in decomposition of toxins while suppressing the toxins from being absorbed.

<2-3> Confirmation of Content of Heavy Metals in Feces, Serum, Liver, and Kidneys Feces were collected from the mice to be tested in <2-1> before 5 o'clock in the afternoon on the next date after the administration was completed, and the contents of lead and cadmium from the serum, liver, and kidneys were confirmed at 5 o'clock. Lead was marked in Table 2, and cadmium was marked in Table 3.

TABLE 2

| Group | Serum | Liver | Kidneys | Feces 1 | Feces 2 | Feces 3 |
|---|---|---|---|---|---|---|
| Normal control | ND | ND | ND | ND | ND | ND |
| Negative control | 0.08 ± 0.01 | 0.23 ± 0.012 | 1.33 ± 0.012 | ND | ND | ND |
| First experimental group | 0.05 ± 0.006 | 0.12 ± 0.01 | 1.02 ± 0.008 | ND | 0.01 ± 0.004 | 0.03 ± 0.006 |
| Second experimental group | ND | 0.05 ± 0.01 | 0.58 ± 0.005 | 0.05 ± 0.007 | 0.04 ± 0.006 | 0.05 ± 0.01 |

TABLE 3

| Group | Serum | Liver | Kidneys | Feces 1 | Feces 2 | Feces 3 |
|---|---|---|---|---|---|---|
| Normal control | ND | ND | ND | ND | ND | ND |
| Negative control | 0.01 ± 0.01 | 1.82 ± 0.04 | 1.55 ± 0.06 | 0.02 ± 0.02 | ND | 0.08 ± 0.05 |
| First experimental group | ND | 0.61 ± 0.02 | 0.73 ± 0.09 | ND | 0.16 ± 0.03 | 0.12 ± 0.08 |
| Second experimental group | ND | 0.37 ± 0.01 | 0.23 ± 0.03 | 0.26 ± 0.06 | 0.21 ± 0.07 | 0.15 ± 0.06 |

When lead is absorbed and accumulated in the human body, there may occur a poisoning phenomenon such as body weight reduction, anemia, biochemical and morphological changes of the organs such as liver and kidneys, and reduction in immunological function. As shown in Table 2, it could be confirmed that lead was accumulated at a high level in the kidneys, and that lead was also more or less accumulated in the liver.

It was confirmed that in the case of the first experimental group, lead was discharged at a low concentration from feces, and that in the case of the second experimental group, lead was discharged at a high concentration in feces. Moreover, it could be confirmed that in the case of the first experimental group, the content of lead was decreased to a statistically significant level in the liver and kidneys. Further, in the case of the second experimental group, an effect of decrease in content of lead by two times or more in the kidneys and liver was confirmed as compared to that of the first experimental group, and lead was not observed in the serum.

Cadmium is a representative heavy metal exhibiting toxins in the liver and kidneys in the organism, and it could be confirmed that cadmium was accumulated at a higher concentration than that of lead in the liver and kidneys. In the case of the first experimental group, it can be confirmed that the concentration of cadmium accumulated in the serum, liver, and kidneys was lower by about 50% than that of the negative control, and in the case of the second experimental group, it can be confirmed that the content of cadmium accumulated in the kidneys is lower by about 85% than that of the negative control, and the content of cadmium accumulated in the liver is lower by 80% than that of the negative control. Further, in the case of the first experimental group and the second experimental group, it can be seen that cadmium is discharged in feces at a high level as compared to that of the negative control.

INDUSTRIAL APPLICABILITY

When a detoxifying composition containing a new green extract according to the present invention as an active ingredient is used, toxicities in the human body can be efficiently removed without side effects by activating the detoxification. Therefore, the composition may be utilized in a functional food or pharmaceutical, and the like having effects such as detoxification.

The invention claimed is:

1. A preparation method of a detoxifying food with new green extract,
    (a) preparing a new green;
    (b) sorting and grinding the new green;
    (c) carrying out an extraction to extract an extract from the ground new green repeatedly one to ten times by using a solvent;
    (d) filtering the extract by a filter cloth to produce a filtrate; and
    (e) concentrating the filtrate under vacuum to produce a new green extract,
    wherein, in step (c), the solvent is one of water with a volume amount (v/w %) which is 1 to 25 times the weight of the ground new green, an alcohol having 1 to 4 carbon atoms, and a mixed solvent thereof; the extraction is performed at 0 to 120° C. for 1 hour to 10 days; and the extraction is performed by cold brew extraction, hot water extraction, ultrasonic extraction, reflux cooling extraction, or heated extraction, and
    the new green extract is capable of activating phase II and phase III in a detoxification process as an active ingredient.

2. A preparation method of a detoxifying food with a complex extract of new green and thistle,
    (a1) preparing a new green and a thistle;
    (b1) sorting and grinding the new green;

(c1) carrying out a first extraction to extract a first extract from the ground new green repeatedly one to ten times by using a first solvent;

(d1) filtering the first extract by a first filter cloth to produce a new green filtrate;

(e1) concentrating the new green filtrate under vacuum to produce a new green extract, wherein, in step (c1), the first solvent is one of water with a volume amount (v/w %) which is 1 to 25 times the weight of the ground new green, an alcohol having 1 to 4 carbon atoms, and a mixed solvent thereof; wherein the first extraction is performed at 0 to 120° C. for 1 hour to 10 days; and the first extraction is performed by cold brew extraction, hot water extraction, ultrasonic extraction, reflux cooling extraction, or heated extraction;

(a2) sorting and grinding the thistle;

(b2) carrying out a second extraction to extract a second extract from the ground thistle repeatedly one to ten times by using a second solvent;

(c2) filtering the second extract by a second filter cloth to produce a thistle filtrate;

(d2) concentrating the thistle filtrate under vacuum to produce a thistle extract, wherein, in step (b2), the second solvent is one of water with a volume amount (v/w %) which is 1 to 25 times the weight of the ground thistle, an alcohol having 1 to 4 carbon atoms, or a mixed solvent thereof; the second extraction is performed at 0 to 120° C. for 1 hour to 10 days; and the second extraction is performed by cold brew extraction, hot water extraction, ultrasonic extraction, reflux cooling extraction, or heated extraction; and (g) mixing the new green extract with the thistle extract to produce a complex extract, wherein the complex extract is capable of activating phase II and phase III in a detoxification process as an active ingredient.

3. The method of claim 1, further comprising, (f) mixing the new green extract with a dextrin.

4. The method of claim 2, further comprising, (f) mixing the new green extract with a first dextrin and mixing the thistle extract with a second dextrin between step (d2) and step (g).

5. The method of claim 1, further comprising (f) lyophilizing the new green extract.

6. The method of claim 2, further comprising, (f) lyophilizing the new green extract and the thistle extract between step (d2) and step (g).

7. The method of claim 3, the ratio of the new green extract and the dextrin is 1:1.

8. The method of claim 4, the ratio of the new green extract and the first dextrin is 1:1 and the ratio of the thistle extract and the second dextrin is 1:1.

9. The method of claim 1, wherein the phase II is activated by an increase in glutathione S-transferase, quinone reductase, and UDP-glucuronosyl transferase.

10. The method of claim 2, wherein the phase II is activated by an increase in glutathione S-transferase, quinone reductase, and UDP-glucuronosyl transferase.

* * * * *